United States Patent [19]
de la Torre

[11] Patent Number: 5,391,176
[45] Date of Patent: Feb. 21, 1995

[54] SURGICAL INSTRUMENT FOR TYING A KNOT IN A LENGTH OF SUTURE AT A REMOTE LOCATION

[75] Inventor: Roger de la Torre, Lake St. Louis, Mo.

[73] Assignee: General Surgical Innovations, Inc., Palo Alto, Calif.

[21] Appl. No.: 71,297

[22] Filed: Jun. 2, 1993

[51] Int. Cl.⁶ ............................................. A61B 17/00
[52] U.S. Cl. ................................... 606/148; 606/139; 606/144
[58] Field of Search .................. 606/1, 139, 144, 147, 606/148, 145; 112/169, 80.03

[56] References Cited

U.S. PATENT DOCUMENTS

| | | |
|---|---|---|
| 1,400,653 | 12/1921 | Barbour . |
| 2,012,776 | 8/1935 | Roeder . |
| 2,566,625 | 9/1951 | Nagelmann ..................... 606/147 |
| 2,595,086 | 4/1952 | Larzelere . |
| 3,856,018 | 12/1974 | Perisse et al. . |
| 3,985,138 | 10/1976 | Jarvik . |
| 4,462,395 | 7/1984 | Johnson ........................ 606/100 |
| 4,602,635 | 7/1986 | Mulhollan et al. . |
| 4,641,652 | 2/1987 | Hutterer et al. ................ 606/148 |
| 4,961,741 | 10/1990 | Hayhurst . |
| 5,084,058 | 1/1992 | Li . |
| 5,087,263 | 2/1992 | Li . |
| 5,129,912 | 7/1992 | Noda et al. . |
| 5,133,723 | 7/1992 | Li et al. . |
| 5,163,946 | 11/1992 | Li . |
| 5,201,744 | 4/1993 | Jones ............................... 606/1 |
| 5,211,650 | 5/1993 | Noda . |
| 5,217,470 | 6/1993 | Weston ........................ 606/148 |
| 5,234,443 | 8/1993 | Phan et al. .................... 606/144 |
| 5,242,459 | 9/1993 | Buelna . |

FOREIGN PATENT DOCUMENTS

| | | | |
|---|---|---|---|
| 0912619 | 5/1954 | Germany | 606/139 |
| 0280778 | 11/1927 | United Kingdom | 112/80.03 |

*Primary Examiner*—Stephen C. Pellegrino
*Assistant Examiner*—Jeffrey A. Schmidt
*Attorney, Agent, or Firm*—Rogers, Howell & Heferkamp

[57] ABSTRACT

A surgical instrument and its method of use facilitate tying of a knot in a length of suture material at a remote surgical location. The instrument is comprised of a rod having a slot at one end and a length of suture wrapped over the rod and slot in a particular pattern. A needle is secured to a free end of the suture and the pattern of wrapping the suture on the rod enables loops of suture to move off the rod end and over the needle to form a throw of a knot in the suture.

22 Claims, 4 Drawing Sheets

SURGICAL INSTRUMENT FOR TYING A KNOT IN A LENGTH OF SUTURE AT A REMOTE LOCATION

BACKGROUND OF THE INVENTION

1. Field of the Invention

The present invention pertains to a surgical instrument for tying a knot in a length of suture at a remote location and the method of using the instrument in tying the knot, 2. Description of the Related Various different types of instruments are known in the prior art for use in tying knots in lengths of suture material. Many of these prior art instruments have been developed with the intent to facilitate tying knots in suture material at surgical sites located in remote areas that are difficult to access. Many prior art instruments are designed for use in surgical procedures where large, deep incision are made into the body. The instruments enable tying knots in sutures deep in the incisions. Many prior art instruments are also designed for use in laparoscopic surgical procedures where small incisions are made and the remote surgical site is accessed through cannulas or tubes. Examples of known instruments employed in tying knots in lengths of suture material are disclosed in the U.S. Patents of Larzelere U.S. Pat. No. 2,595,086, Mulhollan et al. U.S. Pat. No. 4,602,635, Hayhurst U.S. Pat. No. 4,961,741, the U.S. Patents of Li U.S. Pat. Nos. 5,084,058; 5,087,263; and 5,163,946; and the U.S. Patent of Li et al. U.S. Pat. No. 5,133,723.

A common characteristic of many known surgical knot-tying instruments is that they are very complicated to operate and time consuming to set up prior to their use. Moreover, many prior art surgical knot-tying instruments are used in a procedure that involves first tying the knot in a length of suture remote from the surgical location and then moving the loose knot along the length of suture material to a position proximate to the surgical location before the knot is tightened at the surgical location.

SUMMARY OF THE INVENTION

The present invention overcomes disadvantages commonly associated with prior art surgical knot-tying instruments by providing a simplified surgical instrument for tying a knot in a length of suture proximate to a surgical site. More specifically, the surgical instrument of the present invention may be employed in either open incision or laparoscopic surgery procedures to position a needle and a length of suture material proximate to a surgical location and to form one or more stitches with the length of suture material at the surgical location, and then to tie a knot in the length of suture material at the surgical location where the knot is formed from two or more throws of the suture material.

The instrument is basically comprised of an elongate rod having opposite first and second ends. The longitudinal length of the rod is designed to enable the first end of the rod to be inserted through a conventional, laparoscopic cannula to position the rod first end proximate to a surgical location site within a body cavity accessible by the cannula. The second end of the rod projects from the cannula where it is grasped manually to enable manipulation of the rod first end within the body cavity. In alternate embodiments of the invention, the rod has a shortened longitudinal length and is connected to an elongate handle that enables manipulation of the rod within the body cavity through a cannula by manual manipulation of the handle. In this embodiment of the invention, the rod is detachable from the handle for its removal and disposal after use and replacement by a like rod on the handle.

The first end of the rod is provided with an indentation or slot that extends into the interior of the rod from the rod's exterior surface. A length of suture material is provided on the rod first end. The length of suture has a needle secured to its first end and the second end of the suture is secured to the second end of the rod or to the handle, The length of suture is wrapped around the first end of the rod in a specific pattern that provides a plurality loops of the suture material around the first end extending over the slot formed in the rod. A portion of the suture's length extends from the last of the plurality of suture loops formed on the rod first end to the needle at the first end of the suture.

Means are provided on the first end of the rod for releasably holding the needle to the rod first end. In the preferred embodiment, a magnet is encased in the material of the rod adjacent the rod first end, The magnet attracts the needle to the rod end and holds the needle in position on the rod end where it may be easily removed.

In use, the first end of the rod is positioned proximate to a surgical location, the inserting the rod end into an open incision or by inserting the rod first end through the interior of a cannula providing access to a body cavity. With the first end of the rod positioned proximate to the surgical location, the needle is removed from its magnetic attachment to the rod either manually or by gripping the needle with a laparoscopic grasper. One or more stitches are made in the desired positions at the surgical location and in preparation to form a first throw of a knot in the suture material, the needle is inserted into the slot in the rod first end beneath the first loop of suture material formed on the rod end. The needle is held in this position beneath the first loop of suture by the magnetism of the rod first end. The needle is released by the grasper and ten retaken by the grasper at the distal end of the needle projecting from beneath the first suture loop. The needle and the first end of the suture material are ten pulled from the slot and from beneath the first suture loop causing the first loop to move off the first end o the rod. As the needle and first end of the suture are continued to be pulled away from the rod first end, the first loop moves down the length of suture toward the stitch made at the surgical location, forming a first throw of a knot in the suture material securely closing the stitch. This procedure may be repeated as many tis as there are suture loops formed on the rod first end to form a knot of any desired number of throws. When the desired knot is formed at the stitch in the surgical location the two lengths of suture extending from the knot are cut and the knot-tying instrument and needle are removed from the surgical location.

BRIEF DESCRIPTION OF THE DRAWINGS

Further objects and features of the present invention are revealed in the following detailed description of the preferred embodiments of the invention and in the drawing figures wherein.

DESCRIPTION OF THE PREFFERED EMBODIMENTS

Figures 1, 2, 3:
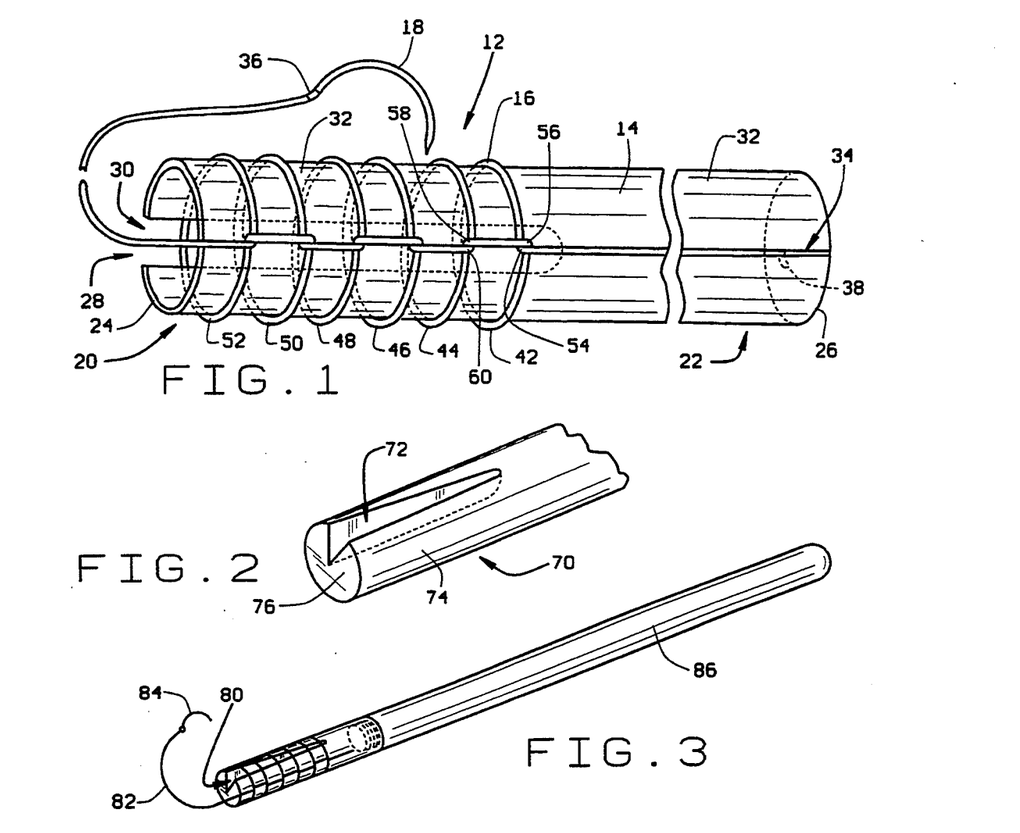
FIG. 1 shows a fragmented perspective view of the surgical instrument for tying a knot in a length of suture.
FIG. 2 shows a partial perspective view of a variant embodiment of the instrument of the invention.
FIG. 3 shows a perspective view of a still further embodiment of the instrument of the invention.
Figure 4:
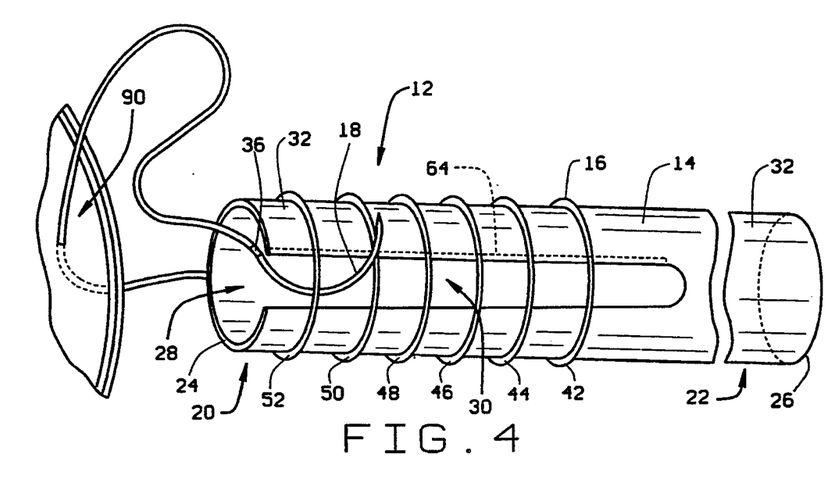
FIG. 4 shows a fragmented perspective view similar to that of FIG. 1 with the instrument of the invention rotated 180°.

A first embodiment of the surgical instrument 12 of the present invention is shown in FIGS. 1 and 4. This first to be described embodiment of the invention, as well as other embodiments of the invention yet to be described, may be constructed of any materials acceptable for use in surgical operations. The instrument is basically comprised of an elongate rod 14, a length of suture material 16 secured to the rod, and a needle 18 secured to the length of suture material.

The elongate rod has opposite first 20 and second 22 ends, or left hand and right hand ends respectively, adjacent opposite first 24 and second 26 end faces, or left and right end faces, as view in FIGS. 1 and 4. A hollow interior bore 28 extends longitudinally through the rod 14 between its end faces 24, 26. The interior and exterior diameter dimensions D the rod 14, as well as its longitudinal length between end faces, may vary depending on the intended application of the instrument. The instrument is designed for use with both open incision surgery and laparoscopic surgery and the rod 14 of the instrument may be dimensioned so that it can be easily inserted through the interior of a cannula in laparoscopic surgery application. Additionally, the lateral dimensions of the instrument rod 14 may be enlarged to further facilitate its use in open incision surgical operations. The dimensions of the rod 14, suture material 16, and needle 18 shown in the drawing figures are not to scale and are rigor proportionate but are enlarged in FIGS. 1 and 4 to better illustrate the component parts of the invention and their relationship to each other. Moreover, i is not necessary that the instrument rod have the cylindrical configuration shown in FIGS. 1 and 4.

A slot 30 is formed through the exterior surface 32 of the rod adjacent its first end 20 forming a recess or indentation into the rod from the exterior surface to the interior bore 28. As seen the drawing figures, the slot 30 extends longitudinally from the first end face 24 of the rod along a port on of the rod's length. A second smaller slot 34 or slit is formed in the second end 22 of the instrument rod extending along a portion of the longitudinal length of the rod from the second end face 26.

The length of suture material 16 has opposite first 36 and second 38 ends with the first end 36 of suture material being secured to the needle 18 in a conventional manner. The total length of the suture material between its first and second ends may vary depending on the intended application of the surgical instrument of the invention, as will be explained. The second end 38 of the suture is secured adjacent the rod second end 26 by inserting the suture into the narrow slot 34. In variant embodiments of the invention, the second end 38 of the suture may be secured to he instrument rod 14 in any equivalent manner, or may be manually held adjacent the rod second end in use of the surgical instrument. The length of suture 16 extends from the instrument rod second end 22 along the exterior surface of the rod toward the rod first end 20 and is wrapped in several loops 42, 44, 46, 48, 50, 52 at the first end 20 of the rod. From the last of the plurality of loops, the suture material extends to its first end 36 secured to the needle 18.

As best seen in FIG. 1 each of the loops of suture material are wrapped around the exterior surface of the rod in a specific configuration that enables individual loops to be spaced from each other along the rod first end 20 and also enables individual loops to be manipulated to slide along the longitudinal length of the rod first end without causing adjacent loops to move along the length of the rod. Although a specific arrangement of the suture material to form the plurality of loops is shown in FIG. 1, it should be appreciated that the suture material 16 may be formed in a variety of different loop configurations on the rod first end 20 that enable the plurality of suture loops to be spaced from each other as shown in FIG. 1 and allow individual loops of suture material to be manually moved longitudinally over the exterior surface of the rod without causing adjacent loops to be moved.

The specific configuration of the suture loops shown in FIG. 1 is produced by forming a first bend 54 in the suture material 16 as it extends longitudinally over the exterior surface of the rod 14 from the second end 22 toward the first end 20 o the rod. From the first bend 54, the suture material extends laterally relative to the rod and is wrapped one complete revolution around the exterior surface of the rod back to the first bend 54. The suture material is hen formed in a second bend 56 around the first bend 54 of the suture and again extends longitudinally along a portion of the rod's length, thereby completing the formation of the first loop 42 in the suture material. The subsequent or adjacent loop 44 is formed in substantially the same manner as the first described loop 42. In forming the second loop, a first bend 58 is formed in the suture material and the suture extends from the first bend laterally around the exterior surface of tile rod 14 one complete revolution back to the first bend of the second loop. Next, a second bend 60 is formed in the suture material around the first bend 58 of the second loop. The suture material continues to extend longitudinally toward the rod first end 20 from the second bend 60, thereby completing the second loop 44 of suture material formed on the exterior of the rod 14. The remaining pairs of loops 46 and 48, 50 and 52, are formed in the suture material as it extends toward the rod first end 20 in the identical manner as the first pair of loops 42, 44 just described.

To illustrate that the loops of suture material formed over the exterior surface of the rod 14 may be formed in a variety of different configurations without departing from the intended scope of the claims of the invention, it is noted that the first and second loops 42, 44 are substantially mirror images of each other, and the second and third loops 44, 46 are also substantially mirror images of each other. In variations of the invention, these first three loops of suture material may have been wound around the exterior surface of the rod 14 so that their configurations are substantially identical to each other, as are the first and third loops 42, 46. Moreover, all of the loops of suture material could have been wrapped around the exterior o the rod 14 in substantially the same configuration as the first loop 42 or all of the plurality of loops cold have been wrapped in substantially the same configuration as the second loop 44 without departing from the intended scope of the claimed invention and without altering the operation of the invention or its method of use.

To prevent the plurality of suture loops from unraveling from the rod first end 20 and to prevent the needle 18 from hanging free from the rod first end a strip magnet 64 is encased in the material of the rod first end extending along one side of the first slot 30 as shown in FIG. 4. By positioning the needle 18 adjacent the side of the slot 30 having the strip magnet 64, the needle is held securely in place at the rod first end 20 as shown in FIG. 4. Alternate means of securing the needle 18 at the rod first end 20 may be employed in place of the strip magnet 64. For example, the rod first end 20 may be formed without the strip magnet 64 and the needle 18 may be positioned between the suture loop 52 formed adjacent the rod first ed face 24 and the exterior surface 32 of the rod to securely hold the needle in place. To prevent the needle tip from projecting from the rod first end the needle may be given a curvature substantially equal to that of the rod exterior surface so that it may be positioned beneath the end loop 52 extending adjacent the rod exterior surface to its tip.

In variant embodiments of the instrument rod 14 the strip magnet 64 could be eliminated from its position adjacent the slot 30 and the needle 18 could be held in place relative to the rod by a conventional laparoscopic surgery grasper inserted through the rod interior bore 28 from its second end 22. The exterior diameter of the rod 14 would be dimensioned small enough to enable it to be inserted through the interior of a conventional laparoscopic cannula. The interior diameter of the rod bore 28 would be dimensioned sufficiently large to enable the insertion of a conventional laparoscopic grasper through the bore. The grasper would be inserted through the rod bore from the rod second end 22 with the jaws of the grasper positioned adjacent he rod first end 20. In this position of the grasper, the jaws would grip and releasably hold the needle 18 on insertion of the first end of the instrument rod through the cannula into the body cavity, and in subsequent manipulations of the needle in forming throws of a knot according to the method of the invention yet to be described. Using the surgical instrument of the invention 12 in this manner also provides the surgeon with a pair of laparoscopic graspers to use together with the instrument in forming stitches laparoscopically without the requirement of inserting more than a pair of cannulas into the body cavity.

In the illustrated embodiment of the invention shown in FIGS. 1 and 4, six suture loops are formed in a length of suture material, and he longitudinal length of the first slot 30 is extended along the length of the rod so that it passes beneath each of the loops formed in the suture material. In variant embodiments of the invention, the number of suture loops may vary and the longitudinal length of the slot beneath the loops may also vary. In use of the invention, it is only necessary that the longitudinal length of the slot be sufficient to enable each of the plurality of loops formed in the suture material to extend over the slot.

FIG. 2 shows a variant embodiment of the rod 70 of the surgical instrument. In tis embodiment, the rod again has a cylindrical configuration; however, the rod does not have a hollow interior bore as in the first embodiment. The rod configuration shown in FIG. 2 is solid with the slot 72 extending down into the interior of the material of the rod from the exterior surface 74. The slot 72, like the slot of the first embodiment, extends for a portion of the longitudinal length of the rod from the rod first end face 76. The longitudinal length of the slot 72 is determined to Enable the slot to extend beneath the plurality of loops formed in suture material (not shown) wrapped over the first end of the rod 70. The remaining component parts, i.e. the suture material and needle, of the second embodiment of the surgical instrument employing the solid rod 70 are substantially identical to those of the first described embodiment of FIGS. 1 and 4.

FIG. 3 shows a still further variant embodiment of the surgical instrument rod 7. In the embodiment of the rod 78 shown in FIG. 3, the first end, or left hand end of the rod as viewed in FIG. 3, may have the same tubular configuration of the first described embodiment of FIG. 1 and 4 or may have the solid configuration of the rod shown in FIG. 2. The rod has a slot 80 formed in its first end in the same manner as the previously described embodiments and a length of suture material is wrapped over the exterior surface of the rod and the slot with one end of the suture secured to the rod and the opposite end of the suture secured to a needle 82 in the same manner as the first described embodiments. The embodiment of FIG. 3 differs from the previously described embodiments in that the longitudinal length of the surgical instrument is divided into two sections with the first section comprising the rod 78 and the second section comprising a handle 86. As shown in FIG. 3, the second end of the rod 78 is detachably secured to one end of the handle 86 by a threaded connection 88. Other equivalent means of providing a releasable connection may also be employed. In this embodiment of the invention, the longitudinal length of the instrument enables it to be used in both deep open incisions or in laparoscopic surgery as in the previously described embodiments. The ability of the rod 78 to be detached from the handle 86 enables the rod to be detached ad disposed of after use and replaced on the handle by a like rod. With the configuration of the surgical instrument shown in FIG. 3, once the length of suture has ben used from one rod of the instrument the used rod may be detached from the handle and replaced with a new rod having a length of suture looped over its exterior surface.

FIGS. 5-10 are schematic representations of the method of the invention employed an using the surgical instrument of the invention for tying a knot in a length of suture in a laparoscopic surgical operation. The drawing figures and their descriptions to follow only generally describe one use of the surgical instrument of the invention and are employed only to illustrate some benefits provided by the surgical instrument of the invention. Drawing FIGS. 5-10 and their descriptions to follow describe use of the surgical instrument of the invention in laparoscopic surgery forming a single stitch to close an incision. Again, it should be understood that the description to follow Is illustrative only and should not be interpreted as limiting the use of the surgical instrument of the invention to only laparoscopic surgical techniques or only use in forming one stitch in securing adjacent tissues together. The benefits provided by the unique surgical instrument of the present invention suit it for use in a variety of different known surgical techniques and for use in forming both a single stitch and a line of stitching in body tissues.

Figure 5:
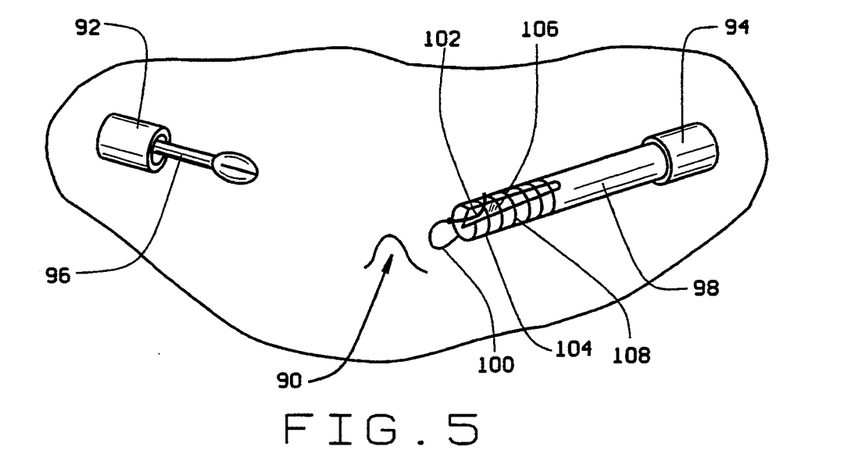
FIG. 5 is a schematic representation of a step involved in the method of use of sloe instrument of the invention in tying a knot in a length of suture in laparoscopic surgery.
Figure 6:
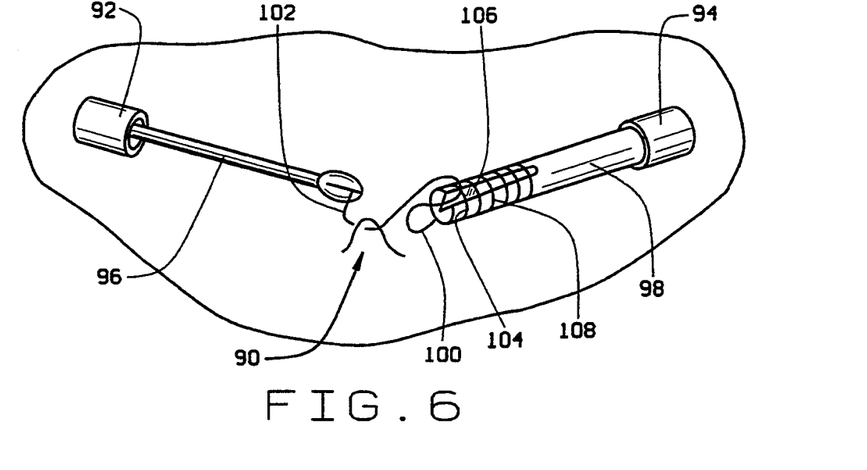
FIG. 6 is a subsequent step to that shown in FIG. 5.
Figure 7:
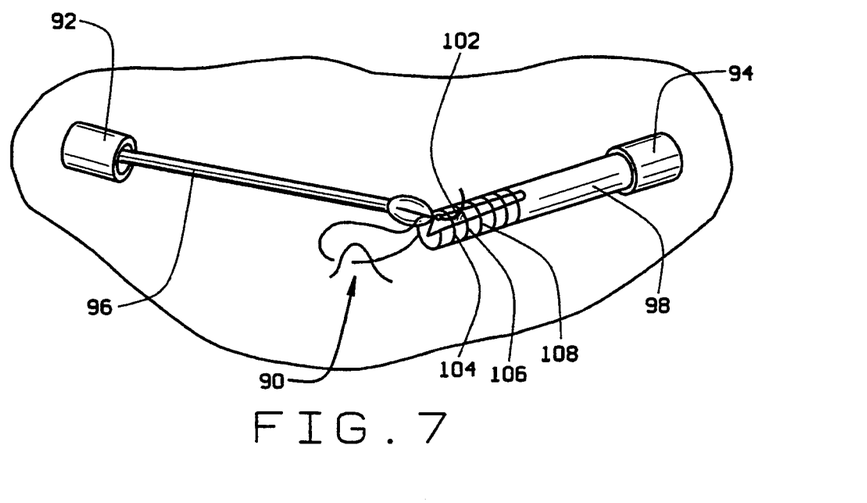
FIG. 7 is a subsequent step to that shown in FIG. 6.
Figure 8:
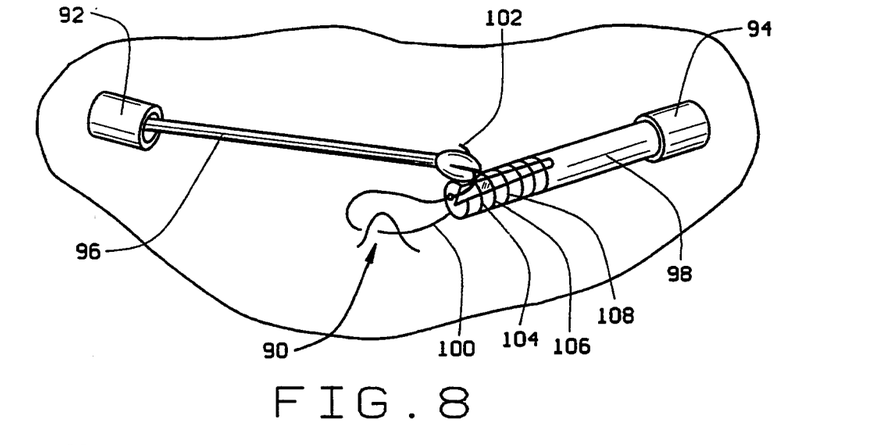
FIG. 8 is a subsequent step to that shown in FIG. 7.

FIG. 5 is a schematic representation of a view looking inside a body cavity toward an opening in a tissue 90 representing a defect to be repaired or mended by use of the surgical instrument of the invention in accordance with the method of the invention. The drawing figure and FIGS. 6–10 to follow illustrate a laparoscopic repair of the defect 90 in the tissue and a pair of trocars 92, 94 are shown already inserted through left and right flanks of the body into the cavity, respectively. Graspers 96 are shown inserted through the left trocar 92 into the body cavity and the first end of the surgical instrument rod 98 with the length of suture 100 wrapped thereover and the needle 102 secured to the suture are shown inserted through the right trocar 94. The needle 102 is shown releasably held to the first end of the instrument rod 98 by a magnet encapsulated in the material of the rod, as was explained earlier. The length of suture extending from the needle 102 to the first suture loop 104 formed on the rod end may be longer than that shown in FIG. 5 to facilitate manipulation of the needle in producing a stitch through the defective tissue 90. The excess length of suture between the needle 102 and the first suture loop 104 may be spirally wound on the rod first end between the rod end face 106 and the first loop 104. In preparing to use the instrument of the invention, the second end of the rod 98 (not shown) extending from the exterior end of the trocar 94 is manipulated to position the rod first end proximate to the surgical location or the defective tissue 90. The graspers 96 are then used to remove the needle 102 from its magnetic attachment to the rod end and a stitch is made through the tissue defect 90 at the surgical location. Only one stitch is shown being made in FIG. 6; however, as explained earlier, the surgical instrument of the invention may be employed informing a line of stitching to close a larger tissue defect. In forming a line of stitching, the needle and attached length of suture are passed through the tissue defect several times along the line in one direction end then are passed again through the tissue defect along e return line back to the position where the suture was first inserted through the tissue. This positions the length of suture extending to the tissue defect from the instrument rod and the length of suture extending from the tissue defect to the needle adjacent each other. With these two lengths of suture positioned adjacent each other a knot may be formed in the suture in the same manner as after forming a single stitch in the tissue defect.

Figure 9:
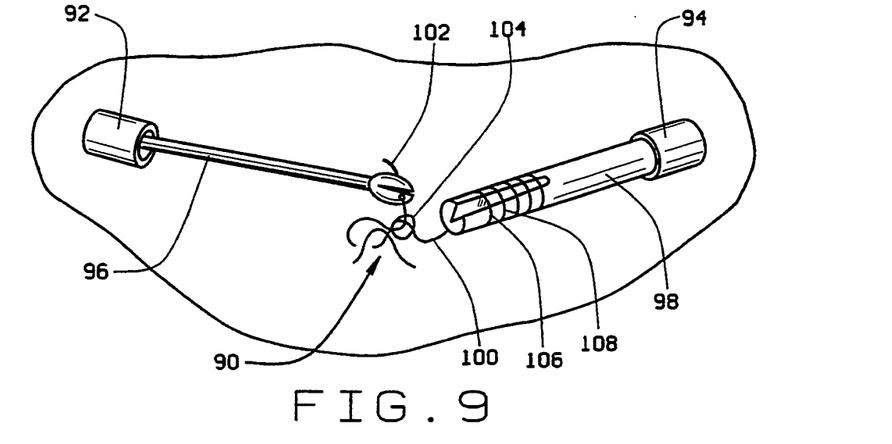
FIG. 9 is a subsequent step to that shown in FIG. 8.
Figure 10:
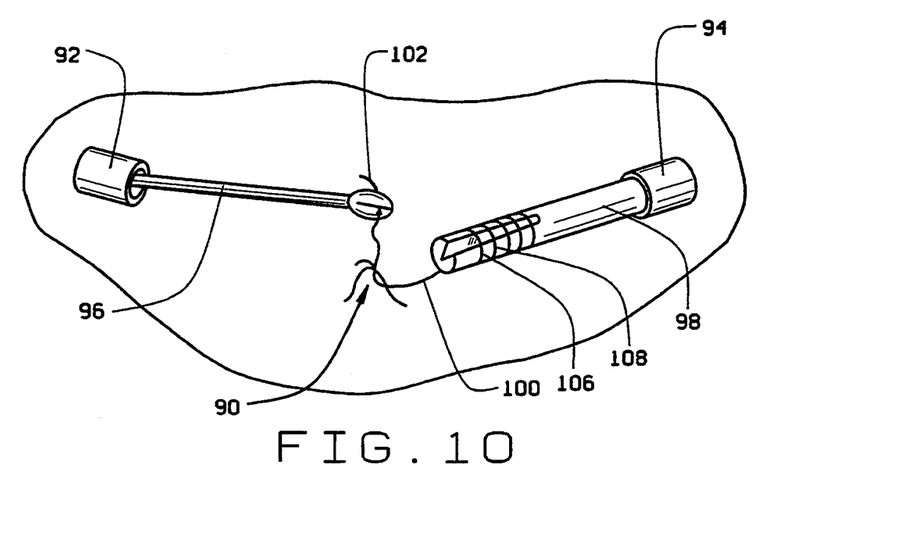
FIG. 10 is a subsequent step to that shown in FIG. 9.

In preparation to form a first throw of a knot in the suture material, the needle is repositioned by the grasper in the slot in the first rod end with the needle extending beneath the first loop 104 of suture material formed on the rod end. FIG. 4 shows in more detail the proper positioning of the needle in preparing to form the first throw of the surgical knot. The needle is held in this position beneath the first loop of the suture by the magnetism of the first rod end. The needle is then released by the grasper 96 and then retaken by the grasper at the distal end of the needle, or the point end of the needle projecting from beneath the first suture loop 104 and out of the slot as viewed in FIG. 8. The needle and attached suture material are then pulled from the instrument slot and from beneath the first suture loop 104 causing the first loop to move off of the first end of the rod as shown in FIG. 9. As the needle and first end of the suture are continued to be pulled away from the rod first end by the rasper, the first loop 104 moves down along the length of suture attached to the needle toward the stitch made at the surgical location in the tissue defect 90, forming a first throw of a knot in the suture material securely closing the stitch, as shown in FIG. 10.

The above process is repeated with the needle and attached suture passing through the slot and beneath the second loop 106 of suture formed on the exterior of the rod first end. As the needle an attached suture are pulled out of the slot and from beneath the second loop 106, the second loop is pulled off the rod first end down the length of suture attached to,the needle. As the needle and attached suture are continued to be pulled away from the rod first end, the second loop arrives at the stitch formed by the first trow and forms a second throw of the knot at the stitch. If so desired, the procedure is repeated a third time by inserting the needle beneath the third loop 108 of suture and pulling the needle from beneath The loop and from the rod first end to cause the third loop to move of the rod end and down the suture forming a third throw in the knot at the stitch. This procedure may be repeated as many times as there are suture loops formed on the rod first end to form a knot of any desired number of throws. When the desired knot is formed at the stitch in the surgical location, the two lengths of suture extending from the knot are cut and the knot-tying instrument and needle are removed from the surgical location.

It should be appreciated that the surgical instrument of the invention facilitates tying a knot in a length of suture material at a remote surgical location according to the method of the invention by enabling the positioning of the suture material proximate to the surgical location and by holding the suture material at the surgical location in a manner that enables one or more throws of a knot to be easily formed in the suture material.

Figure 11:
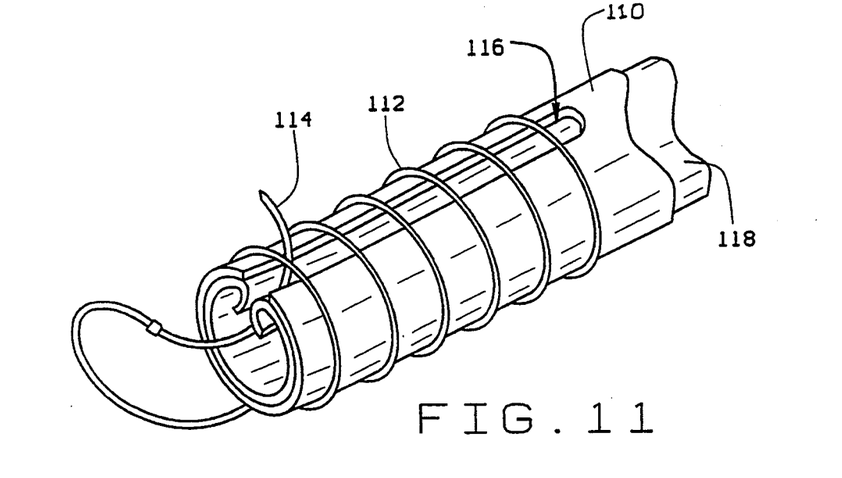
FIG. 11 shows a partial perspective view of a further embodiment of the invention.

FIG. 11 shows a still further embodiment of the rod 110 of the surgical instrument similar to the embodiment shown in FIG. 3. In this embodiment, the rod has substantially the same configuration as the embodiment shown in FIGS. 1 and 4 with the Length of suture material 112 and the needle 114 affixed thereto looped over the exterior surface of the rod 110 in substantially the same manner as that described with reference to FIGS. 1 and 4. The rod 110 has a slot 116 formed in its first end in the same manner as the previously described embodiment of FIGS. 1 and 4 and the length of suture material is looped over the slot. Like the FIG. 3 embodiment, in the FIG. 11 embodiment the longitudinal length of the surgical instrument is divided into two sections, with the first section comprising the rod 110 and the second section comprising a tubular handle 118 having a first end inserted through the interior of the rod. As shown in FIG. 11, the rod 110 is detachably secured to the first end of the handle 118 by being slipfit over the end of the handle. The interior diameter of the rod 110 is substantially equal to the exterior diameter of the handle 118 so tat the rod 110 may be easily slipfit over the end of he handle 118 and held on the handle end by friction engagement. The rod has a slot 120 that is equal in length to the slot 116 of the rod and is aligned with the rod slot. Like the embodiment of FIG. 3, the longitudinal length of the instrument handle 118 enables it to be used in both deep open incisions or in laparoscopic surgery as in the previously described embodiments. The ability of the rod 110 to be detached from the handle 118 enables the rod to be detached and disposed of after use and replaced on the handle by a like rod. With the configuration of the surgical instrument shown in FIGS. 11 and 12, once the length of suture has been used from one rod 110 of the instrument the used rod may be detached from the handle 118 and replaced with a new rod having a length of suture looped over its exterior surface.

Figure 12:
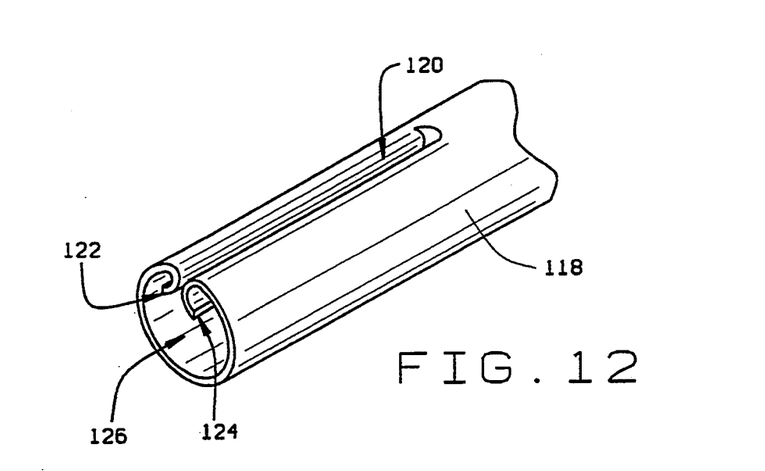
FIG. 12 shows a partial perspective view of a handle used with the embodiment of FIG. 11.

As explained above, the handle slot 120 has a longitudinal length substantially equal to that of the rod slot 116 but is also provided in a specific configuration that enables the handle slot 120 to grip the needle 114 between the opposite lateral ends of the slot. With the handle slot 120 having such an ability, it is no longer necessary to provide a magnetic strip along the slot of the rod 110 to temporarily hold the needle 114 while using the instrument of the of the invention. As best seen in FIG. 12, the opposite lateral ends 122, 124 of the handle slot 120 are curved underneath and then back toward the interior surface of the handle 118. This gives the handle slot 120 a much narrower width than the slot 116 of the rod 110 enabling it to pinch grip the needle 114 within the slot. The manner in which the opposite lateral ends 122, 124 of the handle slot 120 are bent down into the interior bore 126 of the handle 118 forms a pair of tapered converging surfaces in the underside of the slot 120 that direct the needle 114 into the slot 120 when it is inserted into the handle bore 126 from the handle first end and then upward toward the slot. The tapered surfaces of tie underside of the slot 120 direct the tip of the needle 114 inserted into the handle bore 126 upward as viewed in FIG. 12 into the slot 120 thereby facilitating positioning the needle 112 in its gripped stationary position in the slot.

Figure 13:
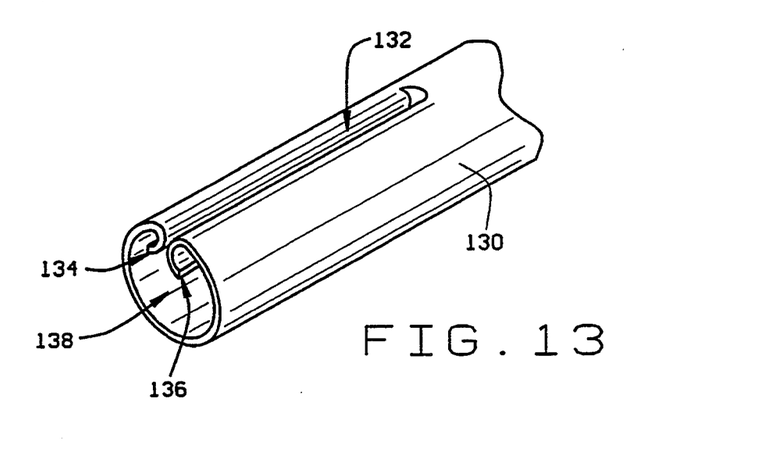
FIG. 13 shows a partial perspective view of a further embodiment of the invention.

A still further embodiment of the rod 130 of the surgical instrument of the investigation is shown in FIG. 13. This embodiment of the rod 130 is substantially identical to the first described embodiment of FIGS. 1 and 4 except for the configuration of the rod slot 132. The first end of the rod 130 has the same cylindrical configuration of the first described embodiment of FIGS. 1 and 4 and although not shown, a length of suture material is wrapped over the exterior surface of the rod and the slot 132 with one end of the suture secured to the rod and the opposite end of the suture secured a needle in the same manner as the first described embodiment. The embodiment of FIG. 13 differs from the previously described embodiment of FIGS. 1 and 4 in that the configuration of the slot 132 is substantially identical to that of the just described embodiment of the instrument handle 118 shown in FIGS. 11 and 12. The instrument rod slot 132 is formed with its opposite lateral edges 134, 136 being downturned into the interior bore 138 of the rod to form the slot configuration shown in FIG. 13. The configuration of the rod slot 132 operates in substantially the suture manner as described above with regard to the handle slot 120 of FIGS. 11 and 12 to direct the needle inserted into the rod bore 138 upward into the slot and to, pinch-grip the needle within the slot. With the configuration of the instrument rod 130 shown in FIG. 13 it would not be necessary to provide a strip magnet adjacent the slot 132 as the function of temporarily holding he needle relative to the rod end is performed by the, configuration of the slot itself.

While the present invention has been described by reference to a specific embodiment, it should be understood that modifications and variations of the invention may be constructed without departing from the scope of the invention defined in the following claims.

What is claimed is:

1. A method of tying a surgical knot in a length of suture at a remote surgery location using a surgical instrument comprising a rod having opposite first and second ends with a slot formed in the first end, and a length of suture with opposite first and second ends wrapped in a plurality of loops around the first end of the rod, the second end of the suture extending to adjacent the second end of the rod and the first end of the suture having a needle secured thereto, the method comprising the steps of:

positioning the rod first end and the needle proximate to the surgery location by manual manipulation of the second end of the rod;

passing the needle and the attached first end of the suture through the surgery location and thereby forming a stitch through the location;

passing the needle and the attached first end of the suture into the slot in the rod first end and beneath a first loop of suture on the rod;

pulling the needle and the attached first end of the suture out of the slot and away from the rod first end, thereby causing the first loop to be pulled off the rod first end and forming a first throw of a knot in the suture at the stitch;

passing the needle and the attached first end of the suture into the slot in the rod first end and beneath a second loop of suture on the rod; and pulling the needle and the attached first end of the suture out of the slot and away from the rod first end, thereby causing the second loop to be pulled off the rod first end and forming a second throw of a know in the suture at the stitch.

2. The method of claim 1, further comprising the step of:

passing the needle and the attached first end of the suture into the slot in the rod first end and beneath a third loop of suture on the rod: and, pulling the needle and the attached first end of the suture out of the slot and away from the rod first end, thereby causing the third loop to be pulled off the rod first end and forming a third throw of a knot in the suture at the stitch.

3. The method of claim 2, further comprising the step of:

after forming the third throw in the knot, cutting the suture first end and second end and removing the needle and the rod from the surgery location.

4. The method of claim 1, wherein the step of:

positioning the rod first end and the needle proximate to the surgery location further includes inserting the rod first end and the needle through a cannula used in a laparoscopic surgery operation.

5. A surgical instrument for tying a knot in a length of suture, the instrument comprising:

a rod having a longitudinal length with opposite first and second ends and an exterior surface extending between the first and second ends;

a slot formed in the first end of the rod;

a length of suture having opposite first and second ends, the first end of the suture being secured to a needle and the second end of the suture being positioned adjacent the second end of the rod, the length of suture extending from its second to its first end along the rod from the rod second end to the rod first end with at least one loop being formed in the suture and wrapped laterally around the exterior surface of the rod and over the slot formed in the first end of the rod, the loop is formed, in the suture by the suture extending longitudinally along the rod from the rod second end toward the rod first end to a first bend formed in the suture intermediate the rod first and second ends and adjacent the slot, the suture next extending laterally relative to the rod from the first bend and wrapping laterally at least one complete revolution around the exterior surface of the rod and over the slot to a second bend formed in the suture engaging around the first bend, and then the suture extending longitudinally relative to the rod from the second bend toward the rod first end and to the needle secured to the suture first end with a sufficient length of the suture provided between the second bend and the needle enabling the needle to pass through a tissue to be ligated and then through the loop formed in the suture thereby tying a knot in the suture.

6. The instrument of claim 5, wherein
the loop is formed in the suture by the suture extending longitudinally along the rod from the rod second end toward the rod first end to the first bend formed in the suture, the suture next extending from the first bend and wrapping laterally one revolution around the exterior surface of the rod and over the slot to the second bend formed in the suture around the first bend, and then the suture extending longitudinally toward the rod first end.

7. The instrument of claim 5, wherein:
a plurality of loops are formed in the suture and are each wrapped laterally around the exterior surface of the rod and over the slot formed in the first end of the rod.

8. The instrument of claim 7, wherein:
each loop of the plurality of loops formed in the suture is formed by the length of suture extending longitudinally along the rod from the rod second end toward the rod first end with a first bend being formed in the suture and the suture extending laterally from the first bend making at least one revolution around the exterior surface of the rod back to the first bend, a second bend being formed in the suture around the first bend and the suture extending longitudinally from the second bend toward the rod first end and subsequent loops of the plurality of loops formed in the suture.

9. The instrument of claim 5, wherein:
a handle having opposite first and second ends is attached to the second end of the rod, the handle having an elongated configuration enabling insertion of the rod and handle through a cannula and to enable manipulation of the rod in laparoscopic surgery by manual manipulation of the handle.

10. The instrument of claim 9, wherein:
the first end of the handle is removably attached to the second end of the rod enabling the rod to be removed from the handle and replaced by a like rod removably attached to the handle first end.

11. The instrument of claim 5, wherein:
the longitudinal length of the rod has an elongated configuration that enables insertion of the first end of the rod through a cannula with the second end of the rod projecting from the cannula enabling remote manipulation of the first end of the rod in laparoscopic surgery by manual manipulation of the rod second end.

12. The instrument of claim 5, wherein:
the slot is configured to enable insertion of the needle secured to the suture first end into the slot and beneath the loop formed in the suture around the exterior surface of the rod, and then removal of the needle from the slot after the needle and the first end of the suture secured thereto have been passed beneath the loop.

13. The instrument of claim 5, wherein:
means are provided on the rod first end for releasably holding the needle to the rod first end.

14. The instrument of claim 13, wherein:
the means for releasably holding the needle to the rod first end includes a magnet secured to the rod first end.

15. A surgical instrument for tying a knot in a length of suture, the instrument comprising:
a rod having a longitudinal length with opposite first and second ends and an exterior surface extending between the first and second ends;
a length of suture having opposite first and second ends, the first end of the suture being secured to a needle and the second end of the suture being positioned adjacent the second end of the rod, the length of suture having at least one loop formed therein, the loop is formed in the suture by the suture extending longitudinally along the rod from the rod second end toward the rod first end to a first bend formed in the suture intermediate the rod first and second ends, the suture next extending laterally relative to the rod from the first bend and wrapping laterally at least one complete revolution around the exterior surface of the rod to a second bend formed in the suture engaging around the first bend, and then the suture extending longitudinally relative to the rod from the second bend toward the rod first end and to the needle secure to the suture first end with a sufficient length of the suture provided between the second bend and the needle enabling the needle to pass through a tissue to be ligated and then through the loop formed in the suture thereby tying a knot in the suture; and
means provided on the rod for enabling the needle to be passed beneath the loop wrapped around the rod pulling the first end of the suture beneath the loop.

16. The instrument of claim 15, wherein:
the longitudinal length of the rod has an elongated configuration that enables insertion of the first end of the rod through a cannula with the second end of the rod projecting from the cannula and enables remote manipulation of the first end of the rod by manual manipulation of the rod second end.

17. The instrument of claim 15, wherein:
a handle is removably attached to the rod second end enabling the rod to be removed from the handle and replaced by a like rod removably attached to the handle, the handle having an elongated configuration enabling insertion of the rod attached to the handle through a cannula in laparoscopic surgery operations with the handle projection from the cannula and enabling remote manipulation of the rod first end by manual manipulation of the handle projecting from the cannula.

18. The instrument of claim 15, wherein:
a plurality of loops are formed in the suture and wrapped around the exterior surface of the rod.

19. The surgical instrument of claim 18, wherein:
each loop of the plurality of loops formed in the suture is formed by the length of suture extending longitudinally along the rod from the rod second end toward the rod first end with a first bend being formed in the suture and the suture extending laterally from the first bend making at least one revolution around the exterior surface of the rod back to the first bend, a second bend being formed in the suture around the first bend and the suture extending longitudinally from the second bend toward the rod first end and subsequent loops of the plurality of loops formed in the suture.

20. The instrument of claim 15, wherein:
the means provided on the rod for enabling the needle to be passed beneath the loop wrapped around the rod includes a recess formed in the exterior surface of the rod beneath the loop.

21. The instrument of claim 20, wherein:
the recess is part of a slot formed in the first end of the rod extending along at least a portion of the longitudinal length of the rod.

22. The instrument of claim 21, wherein:
the loop is formed in the suture by the suture extending longitudinally along the rod from the rod second end toward the rod first end, a first bend being formed in the suture adjacent the slot in the rod first end, the suture from the first bend being wrapped laterally around the exterior surface of the rod and over the slot, then a second bend is formed in the suture around the first bend and the suture extends longitudinally toward the rod first end from the second bend.

* * * * *

UNITED STATES PATENT AND TRADEMARK OFFICE
CERTIFICATE OF CORRECTION

PATENT NO. : 5,391,176  
DATED : February 21, 1995  
INVENTOR(S) : de la Torre, Roger A.

Page 1 of 2

It is certified that error appears in the above-indentified patent and that said Letters Patent is hereby corrected as shown below:

In column 1, at line 12, insert --Art-- after "Related".

In column 2, at line 27 replace "location, the" with --location by--; at line 41 replace "ten" with --then--; at line 44 replace "ten" with --then--; at line 46 replace "o" with --of--; and at line 52 replace "tis" with --times--.

In column 3, at line 7 replace "sloe" with --the--; at line 39 replace "O" with --of--; at line 51 replace "rigor" with --not--; at line 54 replace "i is" with --it is--; and at line 62 replace "port on" with --portion--.

In column 4, at line 9 replace "he" with --the--; at line 39 replace "o" with --of--; and at line 43 replace "hen" with --then--.

In column 5, at line 8 replace "o" with --of--; and at line 63 replace "he" with --the--.

In column 6, at line 6 replace "tis" with --this--; at line 15 replace "Enable" with "enable"; at line 50 replace "ad" with --and--; and at line 58 replace "an" with --in--.

In column 7, at line 1 replace "Is" with --is--; at line 44 replace "informing" with --in forming--; at line 48 replace "end" with --and--; and at line 49 replace "e" with --a--.

In column 8, at line 8 replace "rasper" with --grasper--; at line 20 replace "to,the" with --to the--; at line 23 replace "trow" with --throw--; at line 27 replace "The" with --the--; at line 28 replace "of" with --off--; at line 50 replace "Length" with --length--; and at line 67 replace "tat" with --that--.

In column 9, at line 37 replace "tie" with --the--; at line 63 replace "suture" with --same--; and at line 66 replace "to," with --to--.

UNITED STATES PATENT AND TRADEMARK OFFICE
CERTIFICATE OF CORRECTION

PATENT NO. : 5,391,176

DATED : February 21, 1995

INVENTOR(S) : de la Torre, Roger A.

It is certified that error appears in the above-indentified patent and that said Letters Patent is hereby corrected as shown below:

In column 10, at line 3 replace "the," with --the--.

In column 12, at line 45 replace "secure" with --secured--.

Signed and Sealed this

Fourteenth Day of November, 1995

Attest:

BRUCE LEHMAN

*Attesting Officer*   *Commissioner of Patents and Trademarks*